United States Patent [19]
DesMarais

[11] Patent Number: 6,107,356
[45] Date of Patent: Aug. 22, 2000

[54] HIGH SUCTION POLYMERIC FOAM MATERIALS

[75] Inventor: Thomas Allen DesMarais, Cincinnati, Ohio

[73] Assignee: The Procter & Gamble Company, Cincinnati, Ohio

[21] Appl. No.: 09/378,787

[22] Filed: Aug. 23, 1999

[51] Int. Cl.$^7$ ...................................................... C08J 9/26
[52] U.S. Cl. ............................... 521/62; 521/65; 521/73; 521/142; 521/146; 521/149; 521/150; 524/801; 604/358
[58] Field of Search .................... 521/62, 65, 73, 521/142, 146, 149, 150; 524/801; 604/358

[56] References Cited

U.S. PATENT DOCUMENTS

| | | | |
|---|---|---|---|
| 5,800,416 | 9/1998 | Seger et al. ............................... | 604/366 |
| 5,817,081 | 10/1998 | Lavon et al. ............................... | 604/378 |
| 5,827,253 | 10/1998 | Young et al. ............................... | 604/369 |
| 5,827,909 | 10/1998 | DesMarais ............................... | 523/346 |
| 6,013,589 | 1/2000 | DesMarais et al. ...................... | 442/370 |

Primary Examiner—Samuel A. Acquah
Attorney, Agent, or Firm—Carl J. Roof; Kevin D. Hogg; Steven W. Miller

[57] ABSTRACT

Disclosed are polymeric foam structures suitable for absorbing and storing body fluids such as urine, menses and the like. These liquid storage structures are high suction collapsible polymeric foam materials. The collapsed foams, upon contact with aqueous fluids, can absorb and expand these fluids even when opposed by significant hydrostatic pressures. These absorbent polymeric foams comprise interconnected open-cells. In one aspect, the foams can absorb at least about 25 g/g against a hydrostatic head pressure of 50 cm. In another aspect, the foams of the present invention will have a vertical hang sorption height at 90% of at least about 60 cm.

4 Claims, 4 Drawing Sheets

HIGH SUCTION POLYMERIC FOAM MATERIALS

FIELD OF THE INVENTION

This application relates to high suction polymeric foam materials which are able to absorb aqueous fluids, e.g., urine and menses, when opposed by high pressures. Such foams are particularly useful as storage materials in absorbent articles.

BACKGROUND OF THE INVENTION

The development of highly absorbent articles is the subject of substantial commercial interest. A highly desired characteristic for such products is dryness. This can be achieved by removing the fluid from the proximity of the wearer's skin. Dry diapers, for example, can be more comfortable to wear and less prone to cause skin problems such as rash (diaper dermatitis). The same advantages also accrue for feminine hygiene pads and tampons, adult incontinence briefs, pads for managing perspiration, bandages for wounds, and the like, which generally comprise the class of absorbent articles as worn by humans or animals. Other absorbent articles include items used in construction for leakage prevention, in surgery for blood management, and in horticulture and agriculture for controlled water delivery to plants.

The ability to provide drier absorbent articles such as diapers is contingent on having absorbent cores or structures that can acquire, distribute, and store discharged body fluids such as urine. Such cores can comprise two or more components optimized for the specific function. For example, the core may be a composite of layers which are designed to acquire the fluid quickly to manage gushes or sudden insults, distribute the fluid to regions distant from the point of original insult, and store the fluid by locking it in irreversibly at that distant point.

The art is replete with examples of storage materials, including hydrogel-forming absorbent polymer (hereafter referred to as "HFAPs". These materials are also referred to in the art as "hydrocolloids", "supersorbers" or superabsorbent polymers. The use of such materials is summarized in "Water-Absorbent Polymers: A Patent Survey", Po, R. *J. M. S.— Rev. Macromol. Chem. Phys.* 1994, C34(4), 607–662. Such storage materials are usually blended with a fibrous web in varying proportions for use in absorbent cores. A representative example of such HFAPs are lightly crosslinked polyacrylates. Like many of the other absorbent polymers, these lightly crosslinked polyacrylates comprise a multiplicity of anionic (charged) carboxy groups attached to the polymer backbone. It is these charged carboxy groups that enable the polymer to absorb aqueous body fluids as the result of osmotic forces.

Fluid storage can also be based on capillary forces. Capillary forces are notable in various everyday phenomena, as exemplified by a paper towel soaking up spilled liquids. The art is replete with examples of capillary absorbents formed from fibrous assemblies. Another type of capillary absorbent is sphagnum moss, as described in EP 779,066 (Chauvette et al.) published Jun. 18, 1997. Capillary absorbents can offer superior performance in terms of the rate of fluid acquisition and wicking, i.e., the ability to move aqueous fluid away from the point of initial contact. Indeed, the dual-layer core absorbent structures noted above use the fibrous matrix as the primary capillary transport vehicle to move the initially acquired aqueous body fluid throughout the absorbent core so that it can be absorbed and retained by the HFAP positioned in layers or zones of the core. However such constructions when used as storage elements can fail under pressure leading expressed or free fluid.

The use of absorbent foams in absorbent articles such as diapers has been found highly desirable. If made appropriately, open-celled hydrophilic polymeric foams can provide useful capillary fluid acquisition, transport and/or storage required for use in high performance absorbent cores. Absorbent articles containing such foams can provide desirable wet integrity, sustained body fit, minimize changes in shape during use (e.g., swelling, bunching), and skin dryness. Dryness is achieved by use of layers of foam having differential capillary pressures so that most of the fluid ends up in the layer most distant from the wearer's skin. Examples of these designs are described in U.S. Pat. No. 5,563,129 (infra).

The most useful absorbent foams for absorbent products such as diapers have been made from High Internal Phase Emulsions (hereafter referred to as "HIPEs"). See, for example, U.S. Pat. No. 5,260,345 (DesMarais et al), issued Nov. 9, 1993, U.S. Pat. No. 5,268,224 (DesMarais et al), issued Dec. 7, 1993, U.S. Pat. No. 5,387,207 (Dyer et al.) issued Feb. 7, 1995, U.S. Pat. No. 5,652,194 (Dyer et al.) issued Jul. 29, 1997, U.S. Pat. No. 5,563,179 (Stone et al.) issued Oct. 8, 1996, and U.S. Pat. No. 5,563,129 (supra) and U.S. Pat. No. 5,560,222 (DesMarais et al.) issued Jul. 22, 1997, the disclosure of each is included herein by reference. These absorbent HIPE foams provide generally desirable fluid handling properties, including: (a) relatively good wicking and fluid distribution characteristics to transport the imbibed urine or other body fluid away from the initial impingement zone and into the unused balance of the foam structure to allow for subsequent gushes of fluid to be accommodated; and (b) a relatively high storage capacity with a relatively high fluid capacity under load, i.e., under compressive forces. These HIPE-derived absorbent foams are also sufficiently flexible and soft so as to provide a high degree of comfort to the wearer of the absorbent article, and can be made relatively thin until subsequently wetted by the absorbed body fluid.

While these HIPE-derived foams function very well in appropriately designed absorbent articles, the opportunity for further improvements associated with further advances in absorbent product designs is presented. In an example design, the entire storage element is to be located at a position distant from and relatively higher than the crotch region (referenced to a standing wearer). In diapers, such designs minimize the amount of fluid stored in the sensitive crotch region of the wearer. This not only preserve the original comfortable shape of the diaper, but also allows the crotch region to be thinn than would otherwise be required. Perhaps most importantly, this design can keep crotch region drier for better skin health because the urine is substantially removed from that location by the storage core. This design requires a component within the storage core that is able to drain the acquisition layer and then wick the absorbed fluid by capillary action to some significant height above the insult zone. Exemplary distribution materials are described in more detail in co-pending U.S. patent application Ser. No. 08/042,418, filed Mar. 13, 1998 by DesMarais et al. entitled "ABSORBENT MATERIALS FOR DISTRIBUTING AQUEOUS LIQUIDS" (P&G Case 7051). The storage element is than to be concentrated relatively nearer the wearer's waist than the crotch region. Thus, the product design comprises a relatively open acquisition member able to accept fluid gushes, a distribution layer with sufficient capillary pressure to remove the fluid substantially from the acquisition component and then wick the fluid to the height required before the next fluid insult is likely to have occurred, and a storage layer able to remove the fluid from the distribution layer. (The components are understood generally to be "layers" but can in principle comprise any shape consistent with the functioning of the product.)

The absolute height required in this example is variable depending both on the size of the product and its core and the orientation of the wearer relative to the ground. In general, the height can range from about 12 cm for infants (who are seldom in an upright position) to about 15 to 20 cm for older toddlers and up to about 25 cm for adults. The storage element must be able to at least pull fluid against the hydrostatic head pressure created by these heights. Additionally, however, the storage element must overcome the desorption pressure of the acquisition or distribution layer against which it is positioned. See co-pending U.S. patent application Ser. No. 09/042,418, filed Mar. 13, 1998 by DesMarais et al. entitled "ABSORBENT MATERIALS FOR DISTRIBUTING AQUEOUS LIQUIDS" (P&G Case 7051), which is directed to improved fluid distribution materials. This desorption pressure for any material capable of wicking fluid 20 cm will be greater than 20 cm. The desorption pressure can be twice or more the absorption pressure.

While specific examples will vary, experience has shown that the storage element must be generally able to acquire aqueous fluids of nominal surface tensions against a total pressure (desorption plus gravitational) of at least about 40 cm, preferably at least about 50 cm, more preferably at least about 60 cm, and most preferably at least about 70 cm. In those absorbent articles wherein the crotch region comprises only fluid acquisition and/or distribution materials (i.e., no true storage material), the degree of dryness in the crotch area ultimately achieved is a function of the desorption pressure of the acquisition and/or distribution components, the height of the storage element relative to the acquisition component, and the absorption pressure and capacity of the storage element. Storage elements capable of delivering the capillary pressure necessary to generate a high level of dryness may be generally described as "high suction" elements.

The overall capacity of the storage element is also quite important. While many materials such as fibrous webs may be densified so as to acquire fluids against a total pressure of about 40 to 70 cm, the capacity or void volume of such components is poor, typically less than about 2–3 g/g at 40 cm. Densification also decreases the capacity at 0 cm. Further, such webs tend to collapse under pressure (hydrostatic and mechanical) due to poor mechanical strength, further reducing their effective capacities. Even the absorbent foams described in the art for use as storage components tend to collapse when subjected to pressures equivalent to more than about 30–40 cm of hydrostatic pressure. (Hydrostatic pressure is equivalent to mechanical pressure wherein 1 psi (7 kPa) mechanical pressure is equivalent to about 70 cm of hydrostatic pressure.) This collapse again substantially reduces (usually by a factor of between about 5 and 8) the useful capacity of these foams. While this reduced capacity can in principle be overcome by use of more absorbent material, this is generally impracticable due to cost and thinness considerations.

A third important parameter for a storage material is the ability to stay thin prior to imbibing aqueous fluids, expanding rapidly upon exposure to the fluid. This feature is described in more detail in U.S. Pat. No. 5,387,207, supra. This affords a product which is relatively thin until it becomes saturated with fluid at the end of its wearing cycle. This "thin-until-wet" property is contingent upon the balancing of capillary pressures developed within the foam and foam strength, as described in U.S. Pat. No. 5,387,207, supra.

Another important characteristic of the storage element is the ability to wick fluid within itself. Wherein the overlap between the acquisition or distribution component and the storage element is only partial, the storage component must itself be able to wick fluid throughout itself to be efficient.

Finally, it is desirable that the storage element be sufficiently tough to survive during use and manufacture, sufficiently flexible to be comfortable, and amenable to manufacture using commercially viable procedures for large scale production.

Accordingly, it would be desirable to be able to make an open-celled absorbent polymeric foam material that: (1) shows a relatively high capacity for aqueous fluid it relatively high heights; (2) can be relatively thin and lightweight during normal storage and use until wetted with these body fluids; (3) can wick fluids within itself; (4) has sufficient resiliency, toughness and strength under compressive load to absorb and retain these body fluids; and (5) can be manufactured economically without sacrificing these desired absorbency and mechanical properties to an unacceptable degree.

SUMMARY OF THE INVENTION

The present invention relates to high suction storage materials, in particular high suction collapsible polymeric foam materials. These materials, upon contact with aqueous fluids (in particular aqueous body fluids such as urine), can expand and absorb these fluids even when opposed by significant hydrostatic pressures. These absorbent polymeric foam materials comprise a polymeric foam structure of interconnected open-cells. In one aspect, the foams absorb at least about 25 g/g against a hydrostatic head pressure of 50 cm. That is, the foams will have a vertical wicking absorbent capacity at 50 cm of at least about 25 g/g. Vertical wicking absorbent capacity is the capacity of a section at the specified height within a strip of the foam suspended vertically above a container of test fluid. This is measured in accordance with the procedure described in the Test Methods section below.

In another aspect, the foams of the present invention will have a vertical hang sorption height ("VHSH") at 90% of at least about 60 cm. (A foam's VHSH at 90% is the height within a vertically suspended strip of foam, described above, at which the foam contains 90% of its capacity measured at a height of 0 cm. This is determined in accordance with the procedure described in the Test Methods section below.) The foam further can wick fluid within itself to use its entire volume efficiently. This foam structure is further thin-until-wet, flexible, tough, and can be manufactured commercially.

The present invention further relates to a process for obtaining these high suction absorbent foams by polymerizing a specific type of water-in-oil emulsion or HIPE having an oil phase and a water phase. This process comprises the steps of:

A) forming a water-in-oil emulsion, at a shear rate of not more than about 6000 sec$^{-1}$, from:
  1) an oil phase comprising:
    a) from about 85 to about 98% by weight of a monomer component capable of forming a copolymer having a Tg of about 35° C. or lower, the monomer component comprising:

i) from about 45 to about 70% by weight of at least one substantially water-insoluble monofunctional monomer capable of forming an atactic amorphous polymer having a Tg of about 25° C. or lower;

ii) from about 10 to about 30% by weight of at least one substantially water-insoluble monofunctional comonomer capable of imparting toughness about equivalent to that provided by styrene;

iii) from about 5 to about 25% by weight of a first substantially water-insoluble, polyfunctional crosslinking agent selected from divinylbenzenes, trivinylbenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, tetrakis[2-ethoxyacryloxy]silane, and mixtures thereof; and iv) from 0 to about 15% by weight of a second substantially water-insoluble, polyfunctional crosslinking agent selected from polyfunctional acrylates, methacrylates, acrylamides, methacrylamides, and mixtures thereof; and b) from about 2 to about 15% by weight of an emulsifier component which is soluble in the oil phase and which is capable of forming a stable water-in-oil emulsion, the emulsifier component comprising a primary emulsifier having at least about 40% by weight emulsifying components selected from diglycerol monoesters of branched $C_{16}$–$C_{24}$ fatty acids, linear unsaturated $C_{16}$–$C_{22}$ fatty acids, and linear saturated $C_{12}$–$C_{14}$ fatty acids; sorbitan monoesters of branched $C_{16}$–$C_{24}$ fatty acids, linear unsaturated $C_{16}$–$C_{22}$ fatty acids, linear saturated $C_{12}$–$C_{14}$ fatty acids; diglycerol monoaliphatic ethers of branched $C_{16}$–$C_{24}$ alcohols, linear unsaturated $C_{16}$–$C_{22}$ alcohols, and linear saturated $C_{12}$–$C_{14}$ alcohols, and mixtures thereof; and 2) a water phase comprising an aqueous solution containing: (a) from about 0.2 to about 20% by weight of a water-soluble electrolyte; and (b) an effective amount of a polymerization initiator;

3) a volume to weight ratio of water phase to oil phase in the range of from about 30:1 to about 100:1; and B) polymerizing the monomer component in the oil phase of the water-in-oil emulsion to form a polymeric foam material.

The polymeric foam material can be subsequently dewatered to the extent that a collapsed, polymeric foam material is formed that will re-expand upon contact with aqueous fluids.

The process of the present invention allows the formation of these stronger, more uniform foams from HIPEs. This new process entails changes in the emulsion mixing procedure, detailed below.

DETAILED DESCRIPTION OF THE INVENTION

I. High Suction Polymeric Foams

A. Vertical Wicking Absorbent Capacity and Vertical Hang Sorption Height

In one aspect, the high suction materials of the present invention comprise a polymeric foam structure having a vertical wicking absorbent capacity of at least about 25 g/g at a hydrostatic head pressure of 50 cm. Preferred foams will have a vertical wicking absorbent capacity at a hydrostatic head pressure of 50 cm of at least about 27 g/g, more preferably at least about 30 g/g. Typically, the polymeric foam will have a vertical wicking absorbent capacity at a hydrostatic head pressure of 50 cm of from about 25 to about 90 g/g, more typically from about 27 to about 70 g/g, still more typically from about 30 to about 60 g/g.

In another aspect, the high suction foams of the present invention will have an equilibrium 90% VHSH of at least about 60 cm, preferably at least about 70 cm and more preferably at least about 80 cm. Preferably, the foams will have a 90% VHSH of from about 60 to about 80 cm, more preferably from about 70 to about 90 cm, still more preferably from, about 80 to about 90 cm. While not a requirement, certain foams will have both the vertical wicking absorbent capacity and the 90% VHSH properties described.

The development of a high suction, high capacity storage foam requires five primary features. First, the absorbent foam must have a sufficient open void volume (in its expanded state) so as to absorb a substantial quantity of the aqueous fluid (on a g/g basis). Second, the absorbent foam must have a high surface area per unit volume, from which the high suction is derived. Third, the absorbent foam must be substantially hydroplhilic (having a high adhesion tension described infra). Fourth, the absorbent foam must be thin when dry, expanding quickly when in contact with aqueous fluids such as urine. Fifth, the absorbent foam must have sufficient strength to resist collapse under the combined hydrostatic and mechanical pressures to be endured.

Achieving foams with these capabilities has required development of a new set of properties within the foam, and a process for obtaining the foam. These properties include control of cell size uniformity and high compressive strength. With regard to the former, the present invention provides absorbent foams having a relatively high degree of uniformity of cell sizes. Cells are the major repeating element within the foam and can be characterized by the diameter of the unit from edge to edge in its largest dimension. Without being bound by theory, it is believed that this high degree of uniformity is required to achieve the properties required for their function. Foams with relatively poor cell size uniformity exhibit a range of capillary pressures that can result in parts of the foam being unable to compete for fluid. Greater cell size uniformity has been achieved relative to foams described in the art by modified processing techniques detailed hereinafter.

The present invention also provides foams having a high compressive strength. Strength in compression is important to achieving full function within the absorbent product. The load applied to the absorbent foam comes from two sources. First, the wearer can apply a load through movement or contact with a surface which can squeeze fluid from the foam. Second, the capillary pressures applied by the disposition of the storage element at a height relatively above the insult zone (for a standing wearer) also applies a similar load. These loads can result in the premature collapse of the absorbent foam which inherently reduces its useful capacity by a significant amount, usually from about 4 to 8 times.

B. General Foam Characteristics

Polymeric foams according to the present invention useful in absorbent articles and structures are those which are relatively open-celled. This means the individual cells of the foam are generally in unobstructed communication with adjoining cells. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 3 and 4. For purposes of the present invention, a foam material is "open-celled" if at least 80% of the cells in the foam structure that are at least 1 μm in size are in fluid communication with at least one adjacent cell.

In addition to being open-celled, these polymeric foams are sufficiently hydrophilic to permit the foam to absorb aqueous fluids in the amounts specified hereafter. The internal surfaces of the foam structures are rendered hydrophilic by residual hydrophilizing surfactants left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the Test Methods section of U.S. Pat. No. 5,387,207, supra. Foams which are useful as absorbents in the present invention are generally those which exhibit an adhesion tension value of from about 15 to about 65 dynes/cm, more preferably from about 20 to about 65 dynes/cm, as determined by capillary absorption of synthetic urine having a surface tension of 65±5 dynes/cm.

The polymeric foams of the present invention can be prepared in the form of collapsed (i.e. unexpanded), polymeric foams that, upon contact with aqueous fluids, expand and absorb such fluids. These collapsed polymeric foams are usually obtained by expressing the water phase from the polymerized HIPE foam through compressive forces, and/or thermal drying and/or vacuum dewatering. After compression, and/or thermal drying/vacuum dewatering, the polymeric foam is in a collapsed, or unexpanded state. A process for preparing these "thin-until-wet" absorbent foams is described in U.S. Pat. No. 5,652,194 (supra).

Following compression and/or thermal drying/vacuum dewatering, the collapsed polymeric foam can reexpand when wetted with aqueous fluids. Surprisingly, these polymeric foams remain in this collapsed, or unexpanded, state indefinitely when stored under conditions typical for such products during storage, shipment, display, and before use. After compression, and/or thermal drying/vacuum dewatering to a practicable extent, these polymeric foams have residual water that includes both the water of hydration associated with the hygroscopic, hydrated salt incorporated therein, as well as free water absorbed within the foam. This residual water (assisted by the hydrated salts) is believed to exert capillary pressures on the resulting collapsed foam structure.

An important parameter of these foams is their glass transition temperature (Tg). The Tg represents the midpoint of the transition between the glassy and rubbery states of the polymer. Foams that have a higher Tg than the temperature of use can be very strong but may be very rigid and potentially prone to fracture. Such foams also typically take a long time to recover to the expanded state when wetted with aqueous fluids colder than the Tg of the polymer after having been stored in the collapsed state for prolonged periods. The desired combination of mechanical properties, specifically strength and resilience, typically necessitates a fairly selective range of monomer types and levels to achieve these desired properties.

For foams of the present invention, it is preferred that the Tg of the polymer be at least about 10° C. lower than the in-use temperature. Accordingly, monomers are selected as much as possible that provide corresponding homopolymers having lower Tg's. The Tg is derived from the loss tangent (tan[δ]) vs. temperature curve from a dynamic mechanical analysis (DMA) measurement, as described in the Test Methods section of U.S. Pat. No. 5,633,291 (Dyer et al.) issued May 27, 1997, incorporated herein by reference.

C. Properties of the High Suction Foam Structure

1. Capillary Suction Specific Surface Area and Capillary Absorption Pressure

High surface area and adhesion tension are both important in achieving high suction. "Capillary suction specific surface area" (CSSSA) is, in general, a measure of (he test-liquid-accessible surface area of the polymeric network forming a particular foam per unit mass of the bulk foam material (polymer structural material plus solid residual material). CSSSA is determined both by the dimensions of the cellular units in the foam and by the density of the polymer, and is thus a way of quantifying the total amount of solid surface provided by the foam network to the extent that such a surface participates in absorbency. For purposes of the present invention, CSSSA is determined by measuring the amount of capillary uptake of a low surface tension liquid (e.g., ethanol) which occurs within a foam sample of a known mass and dimensions. CSSSA and adhesion tension are measured using the techniques detailed in U.S. Pat. No. 5,387,207, supra. Ally reasonable alternative method for determining CSSSA or adhesion tension can also be utilized.

The expanded polymeric foams of the present invention useful as absorbents are those that have a CSSSA of at least about 0.1 $m^2$/mL. Typically, the capillary suction specific surface area is in the range from about 0.1 to about 0.6 $m^2$/mL, preferably from about 0.15 to about 0.55 $m^2$/mL, most preferably from about 0.18 to about 0.50 $m^2$/mL. Foams having such CSSSA values can develop a sufficient capillary pressure to keep the foam in a collapsed, unexpanded state until wetted with such aqueous fluids and also develop relatively high capillary pressures.

Capillary absorption pressure is one useful measure of the combined influences of density (void volume or capacity), CSSSA, and adhesion tension. [See P. K. Chatterjee and H. V. Nguyen in "Absorbency," Textile Science and Technology, Vol. 7; P. K. Chatterjee, Ed.; Elsevier:

Amsterdam, 1985; Chapter 2.] For the purposes of the present invention, the capillary absorption pressure of interest is the hydrostatic head at which the vertically wicked fluid loading is 50% of the free absorbent capacity under equilibrium conditions at 31° C. The hydrostatic head is represented by a column of fluid (e.g., synthetic urine) of height h. To be especially useful in absorbent articles for absorbing aqueous fluids, the preferred absorbent foams of the present invention will generally have a capillary absorption pressure of at least about 45 cm, more preferably at least about 55 cm, still more preferably at least about 65 cm. Foams of the present invention typically have absorption pressures of from about 45 cm to about 150 cm, more typically from about 55 to about 120 cm, still more typically from about 65 cm to about 90 cm. Foams described previously in the literature would be collapsed at these pressures and lose most of their effective capacities. For the purposes of measuring a foam's capillary absorption pressure, Applicants use a modified procedure taken from Burgeni, A. A.; Kapur, C. *Textile Research Journal* 1967, 356–366. The method is described in detail in the Test Methods section below.

2. Free Absorbent Capacity

Another important property of the absorbent foams of the present invention is their free absorbent capacity. "Free absorbent capacity" is the total amount of test fluid (synthetic urine) which a given foam sample will absorb into its cellular structure per unit mass of solid material in the sample (under no load or at 0 cm height). To be especially useful in absorbent articles for absorbing aqueous fluids, the absorbent foams of the present invention should have a free absorbent capacity of from about 30 to about 100 mL, preferably from about 30 to about 75 mL, most preferably from about 30 to about 65 mL of synthetic urine per gram of dry foam material. The procedure for determining the free absorbent capacity of the foam is detailed in U.S. Pat. No. 5,563,179 (supra).

3. Expansion Factor

Upon exposure to aqueous fluids, the collapsed foams of the present invention expand and absorb the fluids. For the purposes of the present invention, the relationship between expanded and collapsed thickness for compressively dewatered foams can be empirically predicted from the following equation:

$$Th_{expanded} = Th_{collapsed} \times ((0.133 \times W{:}O \text{ ratio}) \pm 2)$$

where: $Th_{expanded}$ is the thickness of the foam in its expanded state;

$Th_{collapsed}$ is the thickness of the foam in its collapsed state; and

W:O ratio is the water-to-oil ratio of the HIPE from which the foam is made.

Thus, a typical foam made from an emulsion with water-to-oil ratio of 60:1 would have a predicted expansion factor of 8.0 (with a range of 6–10), i.e., an expanded thickness 8 times the collapsed thickness of the foam. The procedure for measuring the expansion factor is described hereafter in the Test Methods section below. The "expansion factor" for these foams is at least about 4x, i.e. the thickness of the foam in its expanded state is at least about 4 times the thickness of the foam in its collapsed state. The collapsed foams preferably have an expansion factor in the range of from about 4x to about 15x, more preferably from about 5x to about 10x.

4. Resistance to Compression Deflection

A relevant feature of the absorbent polymeric foams of the present invention is their strength in their expanded state, as determined by its resistance to compression deflection (RTCD). The RTCD exhibited by the foams herein is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing.

To be useful as high suction storage elements, the foams of the present invention must be suitably resistant to deformation or compression by pressures encountered in use when such absorbent materials are engaged in the absorption and retention of fluids. Foams which do not possess sufficient foam strength in terms of RTCD may not be able to acquire and store acceptable amounts of body fluid from distribution materials when located at heights above the insult zone. Such weak foams will also too easily give up such fluid under the compressive stress caused by the motion and activity of the user of the absorbent articles that contain the foam.

The RTCD exhibited by the polymeric foams of the present invention can be quantified by determining the amount of strain produced in a sample of saturated foam held under a certain confining pressure for a specified temperature and period of time. The method for carrying out this particular type of test is detailed in U.S. Pat. No. 5,563,179 (supra). Foams useful as absorbents are those which exhibit a RTCD such that a confining pressure of 5.1 kPa produces a strain of typically about 20% or less compression of the foam structure when it has been saturated to its free absorbent capacity with synthetic urine having a surface tension of 65±5 dynes/cm. Preferably the strain produced under such conditions will be in the range from about 1 to about 10%, more preferably from about 2 to about 8%, most preferably about 2 to 5%.

5. Cell Size Uniformity

Foam cells are formed by polymerizing a monomer-containing oil phase that surrounds relatively monomer-free water-phase droplets. These cells will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

Figure 3:
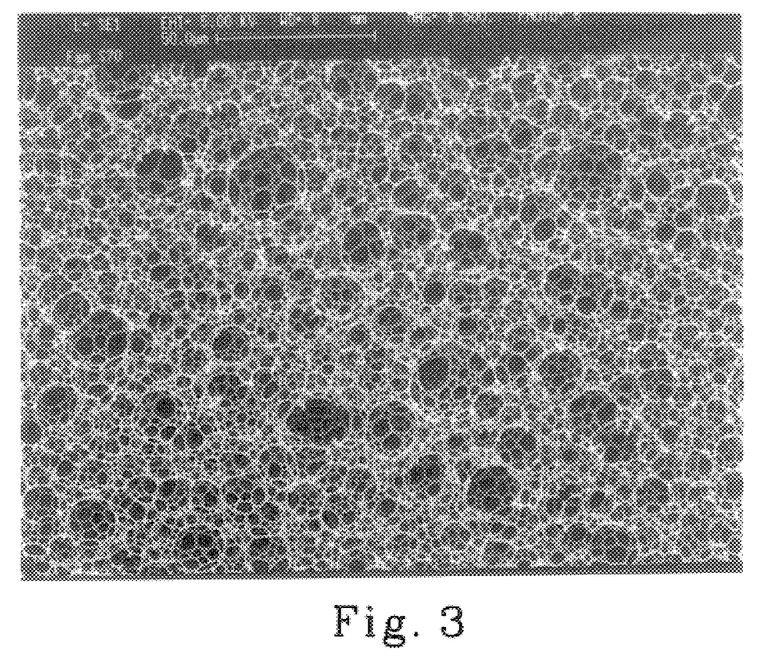
FIG. 3 of the drawings is a photomicrograph (500× magnification) of a high suction polymeric foam of the present invention. The foam is prepared according to Example 2 below.
Figure 4:
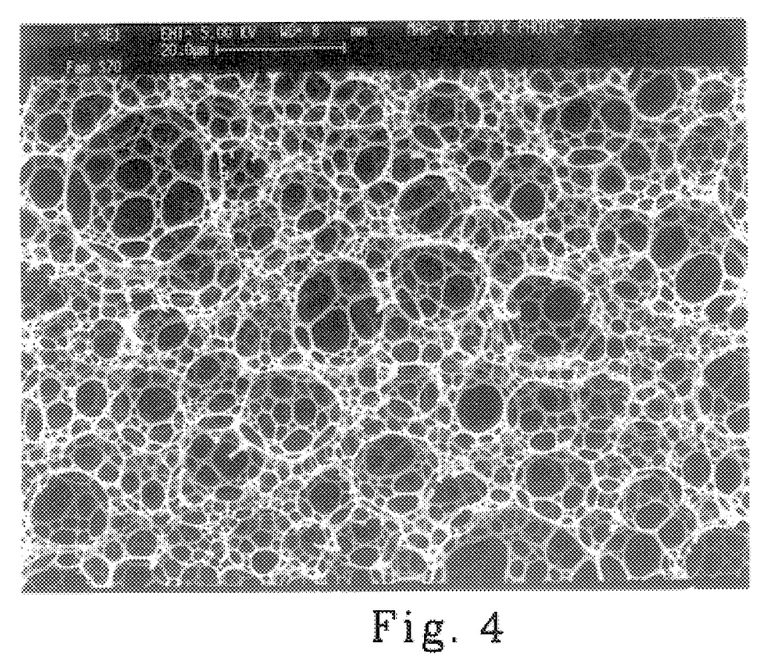
FIG. 4 of the drawings is a photomicrograph (1000× magnification) of the foam of FIG. 3.

A number of techniques are available for determining the average cell size of foams. One useful technique for determining cell size in foams involves a simple measurement based on the scanning electron photomicrograph (SEM) of a foam sample. FIG. 3, for example, shows a typical HIPE foam structure according to the present invention in its expanded state. Superimposed on the photomicrograph is a scale representing a dimension of 50 μm. Such a scale can be used to determine average cell size via an image analysis procedure.

The cell size measurements given herein are based on the number average cell size of the foam in its expanded state, e.g., as shown in FIG. 3. The foams useful as absorbents for aqueous fluids in accordance with the present invention will preferably have a number average cell size of about 50 μm or less, and typically from about 5 to about 25 μm.

6. Other Properties of Foams

"Foam density" (i.e., in grams of foam per cubic centimeter of foam volume in air) is specified herein on a dry basis. The amount of absorbed water-soluble residual materials, e.g., residual salts and liquid left in the foam, for example, after HIPE polymerization, washing and/or hydrophilization, is disregarded in calculating and expressing foam density. Foam density does include, however, other water-insoluble residual materials such as emulsifiers present in the polymerized foam. Such residual materials can, in fact, contribute significant mass to the foam material.

Any suitable gravimetric procedure that will provide a determination of mass of solid foam material per unit volume of foam structure can be used to measure foam density. For example, an ASTM gravimetric procedure detailed in the Test Methods section of U.S. Pat. No. 5,387,207, supra. is one method that can be employed for density determination. In its collapsed state, polymeric foams of the present invention useful as absorbents have dry basis density values in the range of from about 0.1 to about 0.2 g/cc, preferably from about 0.11 to about 0.19 g/cc, and most preferably from about 0.12 to about 0.17 g/cc. In its expanded state, polymeric foams of the present invention useful as absorbents have dry basis density values in the range of from about 0.010 to about 0.032 g/cc, preferably from about 0.013 to about 0.032 g/cc, and most preferably from about 0.015 g/cc to about 0.032 g/cc.

II. Preparation of Polymeric Foams From HIPE

A. In General

Polymeric foams according to the present invention can be prepared by polymerization of certain water-in-oil emulsions having a relatively high ratio of water phase to oil phase commonly known in the art as "HIPEs." Polymeric foam materials which result from the polymerization of such emulsions are referred to hereafter as "HIPE foams." The general procedure for this process is detailed in U.S. Pat. No. 5,563,179 (infra), U.S. Pat. No. 5,571,849, issued to DesMarais on Nov. 5, 1996, and U.S. Pat. No. 5,560,222, issued to DesMarais et al. on Jul. 22, 1997, the disclosure of each of which is incorporated by reference herein. Certain critical variations in this procedure are specified in the Examples section herein.

The relative amounts of the water and oil phases used to form the HIPEs are, among many other parameters, important in determining the structural, mechanical and performance properties of the resulting polymeric foams. In particular, the ratio of water to oil in the emulsion can influence the density, cell size, and capillary suction specific surface area of the foam and dimensions of the struts that form the foam. The emulsions used to prepare the HIPE foams of the present invention will generally have a volume to weight ratio of water phase to oil phase in the range of from about 30:1 to about 100:1, more preferably from about 30:1 to about 75:1, most preferably from about 30:1 to about 65:1.

1. Oil Phase Components

The continuous oil phase of the HIPE comprises monomers that are polymerized to form the solid foam structure. Other oil phase adjuvants include emulsifiers, antioxidants, pigments, and the like, as detailed in U.S. Pat. No. 5,563,179 (infra).

2. Water Phase Components

The discontinuous water internal phase of the HIPE is generally an aqueous solution containing one or more dissolved components. Examples of typical salts, initiators, and other additives are detailed in U.S. Pat. No. 5,563,179 (supra).

3. Hydrophilizing Surfactants and Hydratable Salts

The polymer forming the HIPE foam structure will preferably be substantially free of polar functional groups. This means the polymeric foam will be relatively hydrophobic in character. When these foams are to be used as absorbents for aqueous fluids such as urine, blood, menses, mucous, and other body exudates as well as juice spills, beverages, milk, and the like, they generally require treatment to render the foam relatively more hydrophilic. This can be accomplished by treating the HIPE foam with a hydrophilizing surfactant in a manner detailed in U.S. Pat. No. 5,563,179 (supra), U.S. Pat. No. 5,250,576 (DesMarais et al.) issued Oct. 5, 1993, and U.S. Pat. No. 5,292,777 (DesMarais et al.) issued Mar. 8, 1994, the disclosure of each of which is incorporated herein by reference. Other treatments include chemical modification of the surface as summarized in U.S. Pat. No. 4,536,521 (Haq) issued Aug. 20, 1985 and in Price, G. J.; Clifton, A. A., Keen, F. *Polymer* 1996, 37(26), 5825 and references cited therein and W/O 97/11989 published Apr. 3, 1997, the disclosure of each of which is incorporated by reference.

B. Processing Conditions for Obtaining HIPE Foams

Foam preparation typically involves the steps of: 1) forming a stable high internal phase emulsion (HIPE); 2) polymerizing/curing this stable emulsion under conditions suitable for forming a solid polymeric foam structure; 3) optionally washing the solid polymeric foam structure to remove the original residual water phase from the polymeric foam structure and, if necessary, treating the polymeric foam structure with a hydrophilizing surfactant and/or hydratable salt to deposit any needed hydrophilizing surfactant/ hydratable salt, and 4) thereafter dewatering this polymeric foam structure. These procedures are detailed in U.S. Pat. No. 5,563,179 (infra) and U.S. Pat. No. 5,149,720 (DesMarais et al.), issued Sep. 22, 1992, which is incorporated by reference. See also U.S. Pat. No. 5,827,909 (T. DesMarais), issued Oct. 27, 1998 (herein incorporated by reference), which describes an improved continuous process having a recirculation loop for the HIPE.

Further modifications have been made to the pin impellers so as to achieve the high degree of uniformity in the cell sizes of the foams of the present invention. One preferred method of forming HIPEs having a higher degree of cell uniformity involves a continuous process that combines and emulsifies the requisite oil and water phases. In the mixing chamber or zone (preferably a cylinder), the combined streams are generally subjected to low shear agitation provided, for example, by a pin impeller of suitable configuration and dimensions. The use of low shear agitation provides a higher uniformity of cell sizes in the HIPE, which leads to foams having improved suction capabilities. With a pin impeller of the type used in the present process, both the impeller pin tip speed (hereafter referred to as "tip speed") and the gap between pin tip and the mixing chamber wall (referred to herein as "pin to wall gap", or "gap") are important to shear rate. The shear rate for pin impellers is herein defined as the tip speed divided by the pin to wall gap. For the purposes of this invention this combination variable, shear rate, should be not more than about 6000 $sec^{-1}$. Preferably, shear will typically be applied to the combined oil/water phase stream at a rate of not more than about 5400 $sec^{-1}$, more preferably not more than about 5100 $sec^{-1}$. Typically, the shear rate used will be from about 3000 to about 6000 $sec^{-1}$, more typically from about 3000 to about 5400 $sec^{-1}$, still more typically from about 3300 to about 5100 $sec^{-1}$. Tip speeds should be from about 150 in/sec (381 cm/sec) to about 600 in/sec (1524 cm/sec), preferably from about 150 in/sec (381 cm/sec) to about 500 in/sec (1270 cm/sec), more preferably from about 200 in/sec (508 cm/sec) to about 400 in/sec (1016 cm/sec). Pin to wall gap should be between 1% and 6% of the cylinder diameter, preferably between 1% and 4% of the cylinder diameter, more preferably between 1.5% and 4% of the cylinder diameter.

III. Uses of High Suction Polymeric Foams

The high suction polymeric foams of the present invention are particularly useful is the storage portion of the absorbent structures (e.g., absorbent cores or core elements) for various absorbent articles. By "absorbent article" herein is meant a consumer product that is capable of absorbing significant quantities of urine or other fluids (i.e., liquids), like aqueous fecal matter (runny bowel movements), discharged by an incontinent wearer or user of the article. Examples of such absorbent articles include disposable diapers, incontinence garments, catamenials such as tampons and sanitary napkins, disposable training pants, bed pads, and the like. The absorbent foam structures herein are particularly suitable for use in articles such as diapers, incontinence pads or garments, bed pads, clothing shields, and the like.

In its simplest form, an absorbent article of the present invention need only include a backing sheet, typically relatively liquid-impervious, an acquisition material, and the high suction polymeric foam. The components will be associated such that the acquisition material is closest to the fluid discharge region or insult zone of the wearer of the absorbent article. Next is the high suction polymeric foam backed by the backing sheet. Liquid impervious backing sheets can comprise any material, for example polyethylene or polypropylene, having a thickness of about 1.5 mils (0.038 mm), which will help retain fluid within the absorbent article.

More conventionally, these absorbent articles will also include a liquid-pervious topsheet element that covers the side of the absorbent article that touches the skin of the wearer. In this configuration, the article includes an absorbent core comprising one or mole absorbent foam structures of the present invention positioned between the backing sheet and the topsheet. Liquid-pervious topsheets can comprise any material such as polyester, polyolefin, rayon and the like that is substantially porous and permits body fluid to readily pass there through and into the underlying absorbent core. The topsheet material will preferably have no propensity for holding aqueous fluids in the area of contact between the topsheet and the wearer's skin.

The absorbent core of the absorbent article embodiments of the present invention can consist solely of one or more of these foam structures. For example, the absorbent core can comprise a single unitary piece of foam shaped as desired or needed to best fit the type of absorbent article in which it is to be used. Alternatively, the absorbent core can comprise a plurality of foam pieces or particles that can be adhesively bonded together or which can simply be constrained into an unbonded aggregate held together by an overwrapping of envelope tissue or by means of the topsheet and backing sheet of the absorbent article.

The absorbent core of the absorbent articles herein can also comprise other, e.g., conventional, elements or materials in addition to one or more absorbent foam structures of the present invention. For example, absorbent articles herein can utilize an absorbent core that comprises a combination, e.g., an air-laid mixture, of particles or pieces of the absorbent foam structures herein and conventional absorbent materials such as a) wood pulp or other cellulosic fibers, and/or, b) particles or fibers of HFAP.

In one embodiment involving a combination of the absorbent foam herein and other absorbent materials, the absorbent articles can employ a multi-layer absorbent core configuration where a core layer containing one or more foam structures of the present invention can be used in combination with one or more additional separate core layers comprising other absorbent structures or materials. These other absorbent structures or materials, for example, can include air-laid or wet-laid webs of wood pulp or other cellulosic fibers. These other absorbent structures can also comprise other types of foams, e.g., absorbent foams or even sponges useful as fluid acquisition/distribution components such as those disclosed in U.S. Pat. No. 5,563,179, supra. These other absorbent structures can also contain, for example up to 80% by weight, of particles or fibers of polymeric gelling agent of the type commonly used in absorbent articles that are to acquire and retain aqueous fluids. HFAPs of this type and their use in absorbent articles are more fully described in U.S. Reissue Pat. No. 32,649 (Brandt et al), reissued Apr. 19, 1988, which is incorporated by reference.

An embodiment of these absorbent articles utilizes a multi-layer absorbent core having a fluid handling layer positioned in the fluid discharge region of the wearer of the article. This fluid-handling layer can be in the form of a high loft nonwoven, absorbent foam, or fibrous assembly. One preferred form of a fluid acquisition/distribution layer comprising a layer of modified cellulosic fibers, e.g., stiffened curled cellulosic fibers, and optionally up to about 10% by weight of this fluid acquisition/distribution layer of HFAP. The modified cellulosic fibers used in the fluid acquisition/distribution layer of such a preferred absorbent article are preferably wood pulp fibers that have been stiffened and curled by means of chemical and/or thermal treatment. Such modified cellulosic fibers are of the same type as are employed in the absorbent articles described in U.S. Pat. No. 4,935,622 (Lash et al), issued Jun. 19, 1990, which is incorporated by reference.

A preferred embodiment provides an upper acquisition layer, an intermediate fluid distribution layer such as the type described in co-pending U.S. patent application Ser. No. 09/042,418 filed Mar. 13, 1998 by DesMarais et al. entitled "ABSORBENT MATERIALS FOR DISTRIBUTING AQUEOUS LIQUIDS" (P&G Case 7051) or that described in U.S. Pat. No. 5,800,416 (G. Seger (et al.), issued Sep. 1, 1998 (the disclosure of each of which is incorporated herein by reference), and the high suction polymeric foam of the present invention. For purposes of the present invention, an "upper" layer of a multi-layer absorbent core is a layer that is relatively closer to the body of the wearer, e.g., the layer closest to the article topsheet. The term "lower" layer conversely means a layer of a multi-layer absorbent core that is relatively further away from the body of the wearer, e.g., the layer closest to the article backsheet. This fluid distribution layer is typically positioned between the (upper) fluid-handling and (lower) high suction storage layer and be in fluid communication therewith. Absorbent articles that can utilize the absorbent foam structures of the present invention in a lower fluid storage layer underlying an upper fluid acquisition/distribution layer containing stiffened curled cellulosic fibers are described in greater detail in the U.S. Pat. No. 5,147,345 (Young et al), issued Sep. 15, 1992, incorporated herein by reference. Multi-layer absorbent cores can also be made according to co-pending U.S. application Ser. No. 08/521,556 (G. D. Lavon et al.), filed Aug. 30, 1995, which was abandoned in favor of continuation application Ser. No. 08/883,810, filed Jun. 27, 1997, which issued Oct. 6, 1998 as U.S. Pat. No. 5,817,081 (herein incorporated by reference), where the fluid storage/distribution layers comprises an absorbent foam according to the present invention.

Another preferred embodiment entails a further separation of the various absorbent core elements. This preferred absorbent core comprises an acquisition layer only around the crotch region of the wearer to manage the initial rapid fluid gush. The distribution layer is positioned vertically to the front and back of the acquisition layer so as to wick the fluid out of the crotch region, not just from the front to the back. The storage layer is positioned in a position above the acquisition layer (with an assumed standing position of the wearer) and is in contact only with the distribution material. The storage layer then must be able to absorb the fluid from the distribution layer, overcoming both the force due to gravity and that due to the desorption pressures of the distribution material. The product so depicted removes fluid from the crotch region within the time provided between insults, leaving the acquisition region relatively dry and ready for further uptake of fluid. This further maintains the shape of the garment and keeps the crotch area relatively dry for better skin health.

Figure 1:
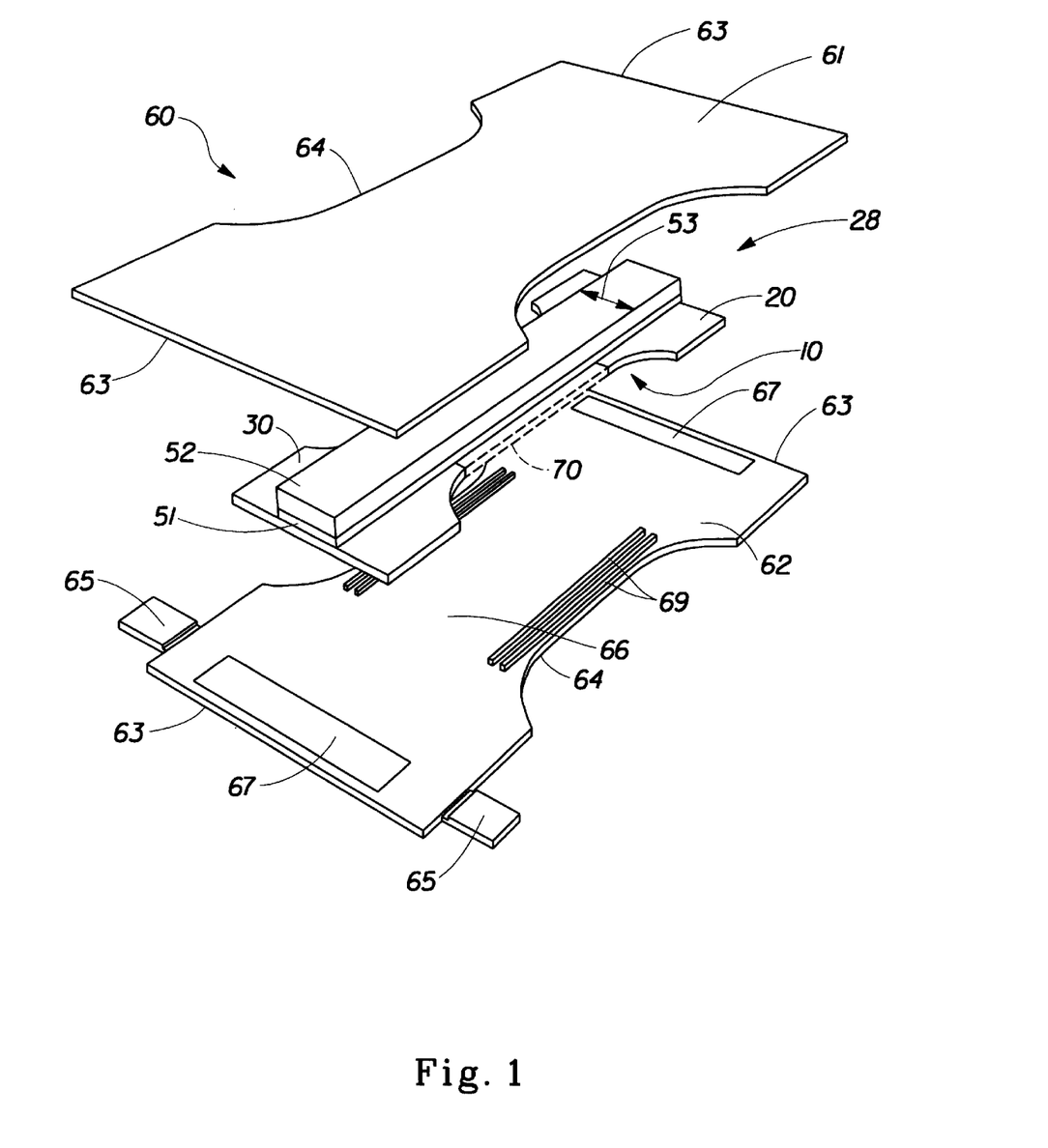
FIG. 1 of the drawings is a blown-apart view of a diaper having an absorbent core which comprises a high capillary suction capacity storage element of the present invention.

FIG. 1 shows a preferred embodiment of a diaper 60 in which the topsheet 61 and the backsheet 62 are co-extensive and have length and width dimensions generally larger than those of the absorbent core 28. The topsheet 61 is joined with and superimposed on the backsheet 62 thereby forming the periphery of the diaper 60. The periphery defines the outer perimeter or the edges of the diaper 60.

The topsheet 61 is compliant, soft feeling, and non-irritating to the wearer's skin. Further, the topsheet 61 is liquid pervious permitting liquids to readily penetrate through its thickness. A suitable topsheet 61 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. In one embodiment, the topsheet 61 is made of a hydrophobic material to isolate the wearer's skin from liquids in the absorbent core 10. A particularly preferred topsheet 61 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet 61. For example, the topsheet 61 can be woven, nonwoven, spunbonded, carded, or the like. A preferred topsheet is carded, and thermally bonded by means well known to those skilled in the fabrics art. Preferably, the topsheet 61 has a weight from about 18 to about 25 grams per square meter, a minimum dry tensile strength of at least about 400 grams per centimeter in the machine direction, and a wet tensile strength of at least about 55 grams per centimeter in the cross-machine direction.

While it is preferred to have a topsheet as the material nearest the wearer's skin, it is not necessary. It is contemplated that a suitable absorbent core configuration could be used without a topsheet and still produce desirable results such as comfort and absorbency as well as simplicity in manufacturing and material cost savings. For example, the body-side surface of the absorbent core itself could be made of liquid pervious, soft, compliant, non-irritating materials that substitute for a separate topsheet. Such an absorbent core would only need to be used in combination with a backsheet to provide for comfort and absorbency in an absorbent article.

The backsheet 62 is impervious to liquids and is preferably manufactured from a thin plastic film, although other flexible liquid impervious materials may also be used. The backsheet 62 prevents the exudates absorbed and contained in the absorbent core 10 from wetting articles which contact the diaper 60 such as bed sheets and undergarments. Preferably, the backsheet 62 is polyethylene film having a thickness from about 0.012 mm (0.5 mil) to about 0.051 centimeters (2.0 mils), although other flexible, liquid impervious materials can be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 62 is preferably embossed and/or matte finished to provide a more clothlike appearance. Further, the backsheet 62 may be "breathable," permitting vapors to escape from the absorbent core 28 while still preventing exudates from passing through the backsheet 62. It is contemplated that a backsheet that is highly breathable but substantially impervious to liquid may be desirable for certain absorbent articles.

The size of the backsheet 62 is dictated by the size of the absorbent core 28 and the exact diaper design selected. In a preferred embodiment, the backsheet 62 has a modified hourglass-shape extending beyond the absorbent core 28 a minimum distance of at least about 1.3 centimeters to at least about 2.5 centimeters (about 0.5 to about 1.0 inch) around the entire diaper periphery.

The topsheet 61 and the backsheet 62 are joined together in any suitable manner. As used herein, the term "joined" encompasses configurations whereby the topsheet 61 is directly joined to the backsheet 62 by affixing the topsheet 61 directly to the backsheet 62, and configurations whereby the topsheet 61 is indirectly joined to the backsheet 62 by affixing the topsheet 61 to intermediate members which in turn are affixed to the backsheet 62. In a preferred embodiment, the topsheet 61 and the backsheet 62 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 61 to the backsheet 62.

Tape tab fasteners 65 are typically applied to the waistband region 63 of the diaper 60 to provide a fastening means for holding the diaper on the wearer. The tape tab fasteners 65 depicted are representative only. The tape tab fasteners can be any of those well known in the art, such as the fastening tape disclosed in U.S. Pat. No. 3,848,594 (Buell), issued Nov. 19, 1974, which is incorporated by reference. These tape tab fasteners or other diaper fastening means are typically applied near the corners of the diaper 60.

Elastic members 69 are disposed adjacent the periphery of the diaper 60, preferably along each longitudinal edge 64, so that the elastic members tend to draw and hold the diaper 60 against the legs of the wearer. Additionally, elastic members 67 can be disposed adjacent either or both of the waistband regions 63 of the diaper 60 to provide a waistband as well as or rather than leg cuffs. For example, a suitable waistband is disclosed in U.S. Pat. No. 4,515,595 (Kievit et al.), issued May 7, 1985, which is incorporated by reference. In addition, a method and apparatus suitable for manufacturing a disposable diaper having elastically contractible elastic members is described in U.S. Pat. No. 4,081,301 (Buell), issued Mar. 28, 1978, which is incorporated by reference.

The elastic members are secured to the diaper 60 in an elastically contractible condition so that in a normally unrestrained configuration, the elastic members effectively contract or gather the diaper 60. The elastic members can be secured in an elastically contractible condition in at least two ways. For example, the elastic members can be stretched and secured while the diaper 60 is in an uncontracted condition. Alternatively, the diaper 60 can be contracted, for example, by pleating, and the elastic members secured and connected to the diaper 60 while the elastic members are in their unrelaxed or unstretched condition. The elastic members may extend along a portion of the length of the diaper 60. Alternatively, the elastic members can extend the entire length of the diaper 60, or any other length suitable to provide an elastically contractible line. The length of the elastic members is dictated by the diaper design.

In use, the diaper 60 is applied to a wearer by positioning one waistband region under the wearer's back, and drawing the remainder of the diaper 60 between the wearer's legs so that the other waistband region is positioned across the front of the wearer. The tape-tab 65 or other fasteners are then secured preferably to outwardly facing areas of the diaper 60. In use, disposable diapers or other absorbent articles incorporating the liquid absorbent members of the present invention tend to more quickly and efficiently distribute and store liquids and to remain dry due to the high absorbent capacity of the liquid absorbent members. Disposable diapers incorporating the liquid absorbent members of the present invention can also be thinner and more flexible.

When used as an absorbent core in a disposable diaper 60, a preferred embodiment of the core 28 according to the present invention is positioned such that an acquisition strip 52 is in liquid communication with topsheet 61, and serves to quickly acquire and partition body exudates from the wearer's body to an absorptive distribution strip 51. Adhesive bonding of acquisition strip 52 to topsheet 61 may enhance the liquid communication by providing interfacial bonding and preventing topsheet separation from impeding liquid flow. A distribution material 51 of the present invention moves liquid in the x and y dimensions of the core 28 and is subsequently desorbed by a liquid storage component comprising a high suction foam of the present invention, shown generally as 10. While components 52 and 51 are shown generally as being rectilinear and of equal size, other shapes and size relationships may be utilized. As shown, the generally rectilinear components have a width 53 corresponding to a suitable width for the crotch area 66 of a disposable diaper. As well, the length of the respective core components may be varied to provide a suitable fit for various wearer sizes. As is shown in FIG. 1, storage component 10 can comprise two separate storage components 20 and 30 comprising the foam of the present invention, such that there is no absorbent storage member element located in the liquid discharge region of the diaper. Because such an absorbent core 10 has little or no liquid storage material (it should be recognized that the distribution material 51 may have significant storage capacity and will contain liquid, at least until it is desorbed by a higher suction storage material of the present invention) in the center of the core (corresponding to the crotch or liquid discharge region of the core), articles containing such cores may provide improved fit and wearer comfort both when the article is dry and after it has received several loadings of body liquid. See, e.g., co-pending U.S. patent application Ser. No. 08/825,072, filed Mar. 27, 1997 by G. Young et al., U.S. Pat. No. 5,827,253 (G. Young et al.), issued Oct. 27, 1998, and co-pending U.S. patent application Ser. No. 08/826,208, filed Mar. 27, 1997 by G. Young et al.

Figure 2A:
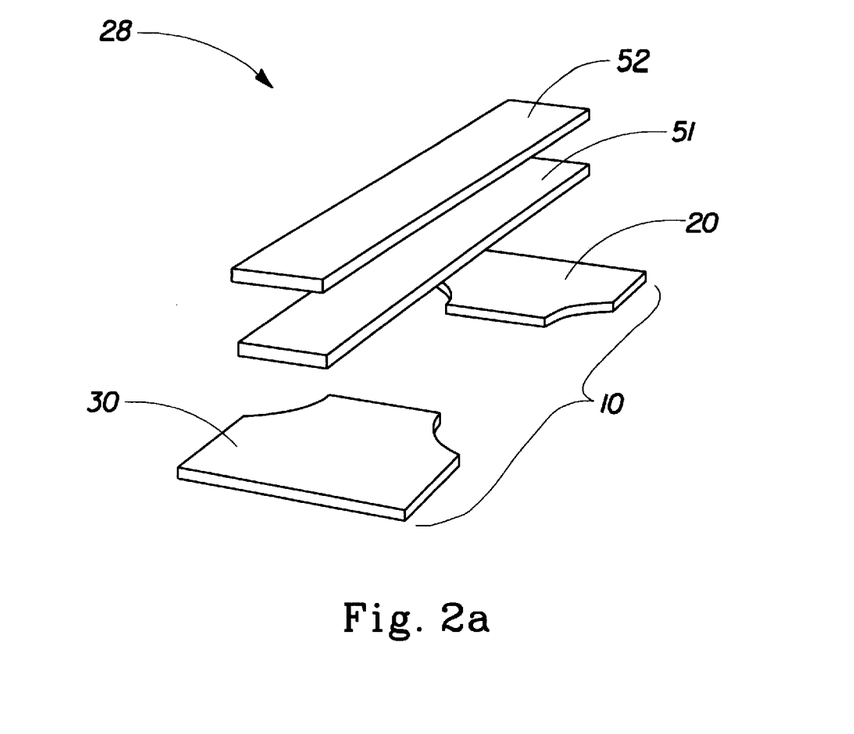
FIG. 2a of the drawings is a blown-apart view of a representative multi-layer core for inclusion in a diaper such as that shown in FIG. 1.

FIG. 2a depicts a blown-apart view of absorbent core 28 having two separated elements 20 and 30, each of which consists of a storage absorbent member comprising a high suction foam of the present invention, wherein those storage elements will desorb distribution material 51. Front panel 20 generally corresponds to the portion of the disposable diaper worn in the front of the wearer. Similarly, the back panel 30 corresponds to the portion of the disposable diaper worn in the back of the wearer. In an alternative design where the absorbent core comprises separate liquid storage elements (similar to elements 20 and 30 in FIG. 1 and FIG. 2a) of the present invention, the distribution layer may be positioned below both the acquisition layer(s) and the storage elements. That is, referring to FIG. 1, distribution material 51 would be located below acquisition) material 52 and storage elements 20 and 30.

Figure 2B:
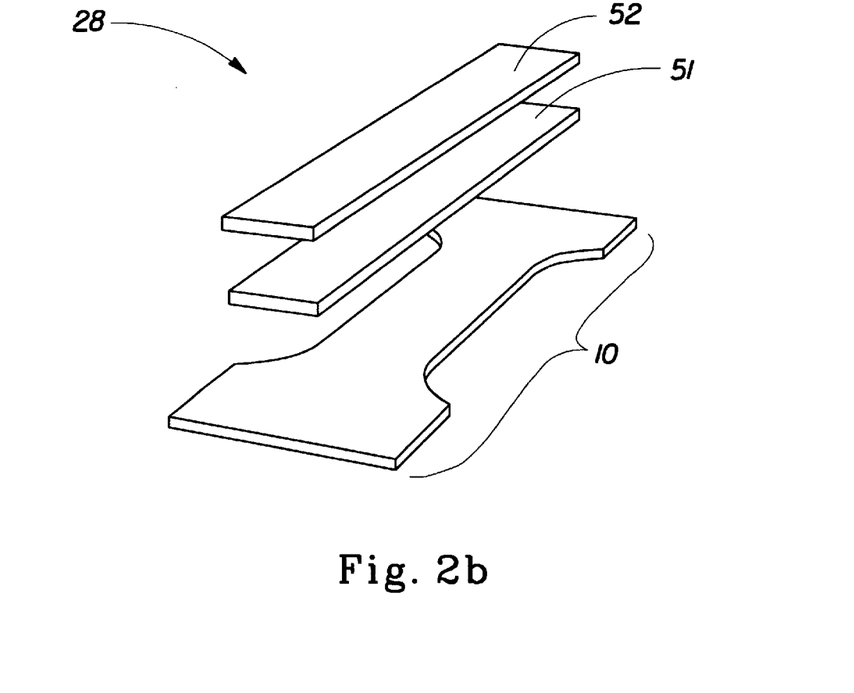
FIG. 2b of the drawings is a blown-apart view of another representative multi-layer core for inclusion in a diaper shown such as that shown in FIG. 1.

Alternatively, storage element 10 may be a unitary layer (s) (i.e., where the dashed lines 70 in FIG. 1 indicate that storage component 10 is included in the liquid discharge region of the article) of absorbent storage material of the present invention. Such an embodiment of an absorbent core 28 is depicted in FIG. 2b.

In one embodiment, acquisition strip 52 will be a liquid handling layer, positioned in the liquid discharge region of the wearer of the article, in the form of a high loft nonwoven, but is preferably in the form of a liquid acquisition comprising a layer of modified cellulosic fibers, e.g., stiffened curled cellulosic fibers, and optionally up to about 10% by weight of this liquid acquisition/distribution layer of polymeric gelling agent. The modified cellulosic fibers used in the liquid acquisition layer 52 of such a preferred absorbent article are preferably wood pulp fibers that have been stiffened and curled by means of chemical and/or thermal treatment. Such modified cellulosic fibers are of the same type as are employed in the absorbent articles described in U.S. Pat. No. 4,935,622 (Lash et al), issued Jun. 19, 1990, which is incorporated by reference. A preferred embodiment is one where the liquid distribution layer 51 is as described in co-pending U.S. patent application Ser. No. 09/042,418 filed Mar. 13, 1998 by DesMarais et al. entitled "ABSORBENT MATERIALS FOR DISTRIBUTING AQUEOUS LIQUIDS" (P&G Case 7051) or U.S. Pat. No. 5,800,416 (G. Seger et al.), issued Sep. 1, 1998, each of which is incorporated by reference herein. This liquid distribution layer is typically positioned between the (upper) liquid-handling and (lower) higher suction storage layer and is in liquid communication therewith.

As referred to herein, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, catamenial pads, sanitary napkins, tampons, bandages, facial tissues, paper towels, and the like.

Another type of absorbent article which can utilize the absorbent foam structures of the present invention comprises form-fitting products such as training pants. Such form-fitting articles will generally include a nonwoven, flexible substrate fashioned into a chassis in the form of briefs or shorts. An absorbent foam structure according to the present invention can then be affixed in the crotch area of such a chassis in order to serve as an absorbent "core". This absorbent core will frequently be over-wrapped with envelope tissue or other liquid pervious, nonwoven material. Such core overwrapping thus serves as the "topsheet" for the form-fitting absorbent article.

The flexible substrate which forms the chassis of the form-fitting article can comprise cloth or paper or other kinds of nonwoven substrate or formed films and can be elasticized or otherwise stretchable. Leg bands or waist bands of such training pants articles can be elasticized in conventional fashion to improve fit of the article. Such a substrate will generally be rendered relatively liquid-impervious, or at least not readily liquid-pervious, by treating or coating one surface thereof or by laminating this flexible substrate with another relatively liquid-impervious substrate to thereby render the total chassis relatively liquid-impervious. In this instance, the chassis itself serves as the "backsheet" for the form-fitting article. Typical training pants products of this kind are described in U.S. Pat. No. 4,619,649 (Roberts), issued Oct. 28, 1986, which is incorporated by reference.

IV. Test Methods

A. Capillary Absorption Pressures

A capillary absorption isotherm curve is generated using the Vertical Wicking Absorbent Capacity test described in the TEST METHODS section of U.S. Pat. No. 5,387,207 (Dyer et al.), issued Feb. 7, 1995, which is incorporated by reference, except the test is performed at 31° C. rather than 37° C. The curve is a plot of the absorbent capacity of each segment as a function of wicked height, using the distance from the top of the water reservoir to the midpoint of each segment for the height h. The capillary absorption pressure is taken as the height of the material that has an absorbent capacity one-half (50%) of the material's free absorbent capacity (i.e., capacity at a height of 0 cm).

B. Vertical Hang Sorption Height (VHSH) and Vertical Wicking Capacity

The Vertical Hang Sorption Height ("VHSH") test is effected by selecting a strip of foam of suitable length (typically at least 60 cm) with a width of typically about 1 cm. The strip is hung in a chamber thermostatted to 31° C. using clips to suspend the strip. The bottom of the strip is immersed in the test fluid, also at 31° C. The test fluid is preferably synthetic urine as described in U.S. Pat. No. 5,599,335 (Goldman et al.) issued Feb. 4, 1997, the disclosure of which is incorporated by reference herein. Over time, the test fluid will wick up the strip and reach an equilibrium point where no further wicking occurs. The test fluid may be dyed to facilitate determination of the equilibrium point. Care must be taken to prevent evaporation from the sample, e.g. by encasing it within a glass tube wherein the glass does not touch the sample, and keeping the sample tube suitably capped. The time required to reach equilibrium may vary for the materials of this invention, and range from about 24 to 96 hrs, or more. When no perceptible change in the height of the wicking fluid is observed over a 1 hour period, equilibrium is assumed to have been achieved.

Figure 5:
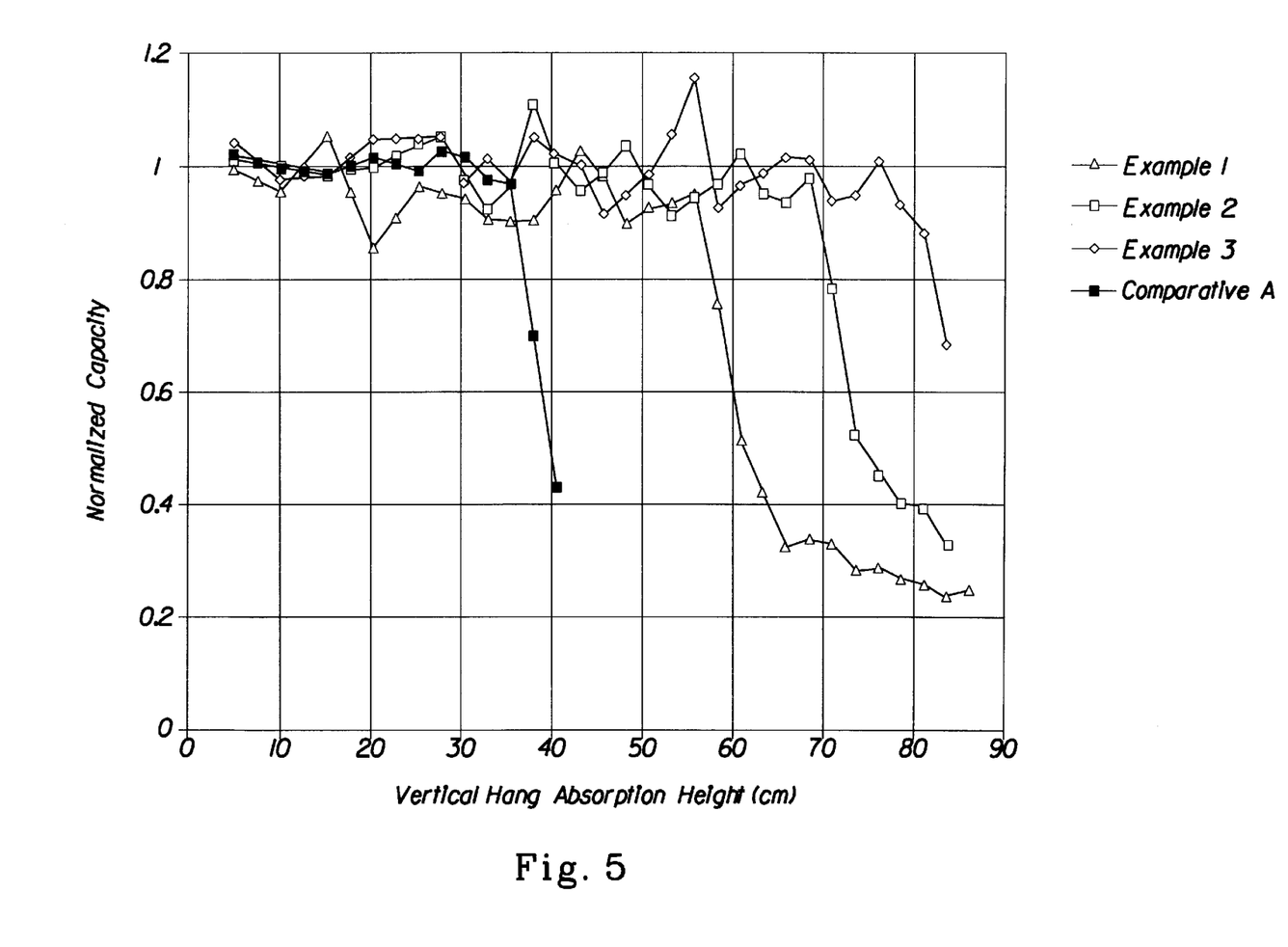
FIG. 5 of the drawings is a vertical hang sorption height curve for three foams of the present invention and one prior art HIPE-derived foam.

The test strip is removed from the test chamber with care to avoid expressing the fluid held therein. The strip is cut into 2.5 cm sections in length and each section is weighed. For convenience, the initial sections below about 50% of the fully expanded height may be cut into sections that are 2 inches (5.1 cm) in length. These weights are divided by the oven dry weight of the foam to compute the capacity (g/g) at the various heights of the foam. A graph such as is depicted in FIG. 5 can be developed by charting the capacities vs. the heights at which the sections were taken, the capacities being divided by the capacity at the first section to obtain a normalized capacity shown in the graph of FIG. 5. The VHSH height at X % is the height in cm where X % of the 0 cm capacity (or FAC) is retained in the foam. A typical value of importance is the VHSH at 90%. In principle, X may be any value. The most reproducible measure for VHSH is achieved at X=90% within the experience of the inventors. It will be obvious to one skilled in the art that this single point value does not fully express the shape of the curve obtained in a plot of capacity vs. height. The single point however serves as a practical point of comparison for the foams of the present invention.

Vertical wicking absorbent capacity at various suction heights can be determined from the VHSH test. See the description of the Vertical Wicking Absorbent Capacity Test described in the Test Methods section of U.S. Pat. No. 5,387,207. (The only modification, as noted above, is that the test is performed at 31° C. instead of 37° C.)

V. Specific Examples

These examples illustrate the specific preparation of collapsed, high suction HIPE foams according the present invention. Physical properties of these prepared foams are summarized in Table 1 below. In addition, normalized capacity vs. Vertical Hang Sorption Height (VHSH) for these foams is shown graphically in FIG. 3. Also shown in Table 1 and on the graph of FIG. 3 are corresponding data for a prior art foam, designated in Table 1 as "comparative example". As can be seen, the foams of the present invention have significantly greater absorptive capacity at relatively high heights (e.g., 50 cm) than do prior art HIPE-derived foams. The foams of the present invention also have significantly higher 90% VHSH values than do prior art foams.

Example 1

Preparation of Foam from a HIPE

A) HIPE Preparation

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a diglycerol monooleate emulsifier (480 g), ditallow dimethyl ammonium methyl sulfate (80g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (53°–55° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shalt holds 6 rows of pins, 3 rows having 33 pins and 3 rows having 34 pins, each of the three pins at each level disposed at an angle of 120° to each other, with the next level down disposed at 60° to its neighboring level with each level separated by 0.03 mm, each having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure of U.S. Pat. No. 5,827,909 (T. DesMarais), issued Oct. 27, 1998, the disclosure of which is incorporated by reference herein. The Waukesha pump in the recirculation zone returns the minor portion to the entry point of the oil and water phase flow streams to the dynamic mixing zone.

The static mixer (TAH Industries Model 100-812) has 12 elements with a 1 inch (2.5 cm) outside diameter. A hose is mounted downstream from the static mixer to facilitate delivery of the emulsion to the device used for curing. Optionally an additional static mixer is used to provide addition back pressure to keep the those filled. The optional static mixer can be a 1 inch (2.5 cm) pipe, 12 element mixer (McMaster-Carr Model 3529K53).

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 cc/sec water phase.

Once the apparatus set-up is filled, agitation is begun in the dynamic mixer, with the impeller turning at 1750 RPM and recirculation is begun at a rate of about 30 cc/sec. The flow rate of the water phase is then steadily increased to a rate of 151.3 cc/sec over a time period of about 1 min., and the oil phase flow rate is reduced to 3.03 g/sec over a time period of about 3 min. The recirculation rate is steadily increased to about 150 cc/sec during the latter time period. The back pressure created by the dynamic zone and static mixers at this point is about 19.9 PSI (137 kPa), which represents the total pressure drop) of the system. The Waukesha pump (Model 30) speed is then steadily decreased to a yield a recirculation rate of about 75 cc/sec.

B) Polymerization of HIPE

The HIPE flowing from the static mixer at this point is collected in a round polyethylene tub, 40 in. (102 cm) in diameter and 12.5 in. (31.8 cm) high, with removable sides, much like a springform pan used in cooking cakes. A pipe-like polyethylene insert 12.5 in (31.8 cm) in diameter at its base is firmly affixed to the center of the base and is 12.5 in (31.8 cm) high. The HIPE-containing tubs are kept in a room maintained at 65° C. for 18 hours to effect polymerization and form the foam.

C) Foam Washing and Dewatering

The cured HIPE foam is removed from the curing tubs. The foam at this point has residual water phase (containing dissolved emulsifiers, electrolyte, initiator residues, and initiator) about 48–52 times (48–52×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% $CaCl_2$ solution at 60° C., are squeezed in a series of 3 porous nip rolls equipped with vacuum to a water phase content of about 4×. The $CaCl_2$ content of the foam is between 8 and 10%.

The foam remains compressed after the final nip at a thickness of about 0.021 in. (0.053 cm). The foam is then dried in air for about 16 hours. Such drying reduces the moisture content to about 9–17% by weight of polymerized material. At this point, the foam sheets are very drapeable and are "thin-after-drying".

Example 2

Preparation of Foam from a HIPE

A) HIPE Preparation

The water and oil phase streams to be used in a continuous process for forming a HIPE emulsion is prepared according to Example 1. Separate streams of the oil phase (25° C.) and water phase (53°–55° C.) are fed to a dynamic mixing apparatus as detailed in Example 1.

Once the apparatus set-up is filled, agitation is begun in the dynamic mixer, with the impeller turning at 1700 RPM and recirculation is begun at a rate of about 30 cc/sec. The flow rate of the water phase is then steadily increased to a rate of 151.3 cc/sec over a time period of about 1 min., and the oil phase flow rate is reduced to 3.36 g/sec over a time period of about 3 min. The recirculation rate is steadily increased to about 150 cc/sec during the latter time period. The back pressure created by the dynamic zone and static mixers at this point is about 19.7 PSI (136 kPa), which represents the total pressure drop of the system. The Waukesha pump speed is then steadily decreased to a yield a recirculation rate of about 75 cc/sec.

B) Polymerization of HIPE

The HIPE flowing from the static mixer at this point is collected and cured into a polymeric foam as detailed in Example 1.

C) Foam Washing and Dewatering

The cured HIPE foam is removed from the curing tubs. The foam at this point has residual water phase (containing dissolved emulsifiers, electrolyte, initiator residues, and initiator) about 43–47 times (43–47×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% $CaCl_2$ solution at 60° C., are squeezed in a series of 3 porous nip rolls equipped with vacuum to a water phase content of about 4×. The $CaCl_2$ content of the foam is between 8 and 10%.

The foam remains compressed after the final nip at a thickness of about 0.028 in. (0.071 cm). The foam is then dried in air for about 16 hours. Such drying reduces the moisture content to about 9–17% by weight of polymerized material. At this point, the foam sheets are very drapeable and are "thin-after-drying".

Example 3

Preparation of Foam from a HIPE

A) HIPE Preparation

The water and oil phase streams to be used in a continuous process for forming a HIPE emulsion is prepared according to Example 1. Separate streams of the oil phase (25° C.) and water phase (53°–55° C.) are fed to a dynamic mixing apparatus as detailed in Example 1.

Once the apparatus set-up is filled, agitation is begun in the dynamic mixer, with the impeller turning at 1750 RPM and recirculation is begun at a rate of about 30 cc/sec. The flow rate of the water phase is then steadily increased to a rate of 151.3 cc/sec over a time period of about 1 min., and the oil phase flow rate is reduced to 3.78 g/sec over a time period of about 3 min. The recirculation rate is steadily increased to about 150 cc/sec during the latter time period. The back pressure created by the dynamic zone and static mixers at this point is about 18.7 PSI (129 kPa), which represents the total pressure drop of the system. The Waukesha pump speed is then steadily decreased to a yield a recirculation rate of about 75 cc/sec.

B) Polymerization of HIPE

The HIPE flowing from the static mixer at this point is collected and cured into a polymeric foam as detailed in Example 1.

C) Foam Washing and Dewatering

The cured HIPE foam is removed from the curing tubs. The foam at this point has residual water phase (containing dissolved emulsifiers, electrolyte, initiator residues, and initiator) about 38–42 times (38–42×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% $CaCl_2$ solution at 60° C., are squeezed in a series of 3 porous nip rolls equipped with vacuum to a water phase content of about 4×. The $CaCl_2$ content of the foam is between 8 and 10%.Q The foam remains compressed after the final nip at a thickness of about 0.028 in. (0.071 cm). The foam is then dried in air for about 16 hours. Such drying reduces the moisture content to about 9–17% by weight of polymerized material. At this point, the foam sheets are very drapeable and are "thin-after-drying".

TABLE 1

|  | W:O Ratio (mL/g) | Capillary Absorption Pressure (cm) | Capacity at 50 cm (g/g) | Equilibrium 90% VHSH (g/g) |
| --- | --- | --- | --- | --- |
| Example 1 | 50:1 | 62 | 45 | 60 cm |
| Example 2 | 45:1 | 74 | 38 | 70 cm |
| Example 3 | 40:1 | 85** | 35 | 80 cm |
| Comparative Example* | 60:1 | 40 | 22*** | 36 cm |

*This foam is prepared in substantially the same manner as the foam of Example 2 in U.S. Pat. No. 5,650,222, except the oil phase is modified to consist of the same components as Examples 1–3 above.
**Projected value
***Value at 41 cm - reasonable projection is 20 g/g at 50 cm.

What is claimed is:

1. A process for making a collapsible polymeric foam structure of interconnected open-cells which, upon contact with aqueous fluids, can expand and absorb the fluids, the process comprising the steps of:
   A) forming a water-in-oil emulsion, at a shear rate of not more than about 6000 $sec^{-1}$, from:
   1) an oil phase comprising:
      a) from about 85 to about 98% by weight of a monomer component capable of forming a copolymer having a Tg of about 35° C. or lower, the monomer component comprising:
         i) from about 45 to about 70% by weight of at least one substantially water-insoluble monofunctional monomer capable of forming an atactic amorphous polymer having a Tg of about 25° C. or lower;
         ii) from about 10 to about 30% by weight of at least one substantially water-insoluble monofunctional comonomer capable of imparting toughness about equivalent to that provided by styrene;
         iii) from about 5 to about 25% by weight of a first substantially water-insoluble, polyfunctional crosslinking agent selected from divinylbenzenes, trivinylbenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, tetrakis[2-ethoxyacryloxy]silane, and mixtures thereof; and
         iv) from 0 to about 15% by weight of a second substantially water-insoluble, polyfunctional crosslinking agent selected from polyfunctional acrylates, methacrylates, acrylamides, methacrylamides, and mixtures thereof; and
      b) from about 2 to about 15% by weight of an emulsifier component which is soluble in the oil phase and which is capable of forming a stable water-in-oil emulsion, the emulsifier component comprising a primary emulsifier having at least about 40% by weight emulsifying components selected from diglycerol monoesters of branched $C_{16}$–$C_{24}$ fatty acids, linear unsaturated $C_{16}$–$C_{22}$ fatty acids, and linear saturated $C_{12}$–$C_{14}$ fatty acids; sorbitan monoesters of branched $C_{16}$–$C_{24}$ fatty acids, linear unsaturated $C_{16}$–$C_{22}$ fatty acids, linear saturated $C_{12}$–$C_{14}$ fatty acids; diglycerol monoaliphatic ethers of branched $C_{16}$–$C_{24}$ alcohols, linear unsaturated $C_{16}$–$C_{22}$ alcohols, and linear saturated $C_{12}$–$C_{14}$ alcohols, and mixtures thereof; and
   2) a water phase comprising an aqueous solution containing: (a) from about 0.2 to about 20% by weight of a water-soluble electrolyte; and (b) an effective amount of a polymerization initiator;
   3) a volume to weight ratio of water phase to oil phase in the range of from about 30:1 to about 100:1; and
   B) polymerizing the monomer component in the oil phase of the water-in-oil emulsion to form a polymeric foam material.

2. The process of claim 1, wherein the water-in-oil emulsion is formed at a shear rate of not more than about 5400 $sec^{-1}$.

3. The process of claim 2, wherein the water-in-oil emulsion is formed at a shear rate of not more than about 4800 $sec^{-1}$.

4. The process of claim 1, wherein the water-in-oil emulsion is formed at a shear rate of from about 3000 to about 6000 $sec^{-1}$.

* * * * *

UNITED STATES PATENT AND TRADEMARK OFFICE
CERTIFICATE OF CORRECTION

PATENT NO.    : 6,107,356
DATED         : August 22, 2000
INVENTOR(S)   : DesMarais It is certified that error appears in the above-identified patent and that said Letters Patent is hereby corrected as shown below:

Column 2,
Line 49, please delete "preserve" and insert therefor -- preserves --.
Line 51, please delete "thinn" and insert therefor -- thinner --.
Line 52, between "keep" and "crotch" please insert therefor -- the --.
Line 63, please delete "than" and insert therefor -- then --.

Column 4,
Line 18, please delete "it" and insert therefor -- at --.

Column 6,
Line 42, please delete "hydroplhilic" and insert therefor -- hydrophilic --.

Column 8,
Line 37, please delete "(he" and insert therefor -- the --.
Line 51, please delete "Ally" and insert therefor -- Any --.

Column 13,
Line 6, please delete "is" and insert therefor -- as --.
Line 36, please delete "mole" and insert therefor -- more --.

Column 17,
Line 64, please delete "Ser. No. 08/826,208" and insert therefor
-- Ser. No. 08/825,071--.
Line 65, please delete "G. Young" and insert therefor -- G. LaVon --.

Column 20,
Line 24, please delete "FIG. 3" and insert therefor -- FIG. 5 --.
Line 25, please delete "FIG. 3" and insert therefor -- FIG. 5 --.
Line 63, please delete "shalt" and insert therefor -- shaft --.

UNITED STATES PATENT AND TRADEMARK OFFICE
CERTIFICATE OF CORRECTION

PATENT NO.    : 6,107,356 B1
DATED         : August 22, 2000
INVENTOR(S)   : DesMarais It is certified that error appears in the above-identified patent and that said Letters Patent is hereby corrected as shown below:

Column 21,
Line 19, please delete "those" and insert therefor -- hose --.

Signed and Sealed this

Fourth Day of February, 2003

JAMES E. ROGAN
*Director of the United States Patent and Trademark Office*